(12) United States Patent
Sattur et al.

(10) Patent No.: US 7,737,146 B2
(45) Date of Patent: Jun. 15, 2010

(54) COMPOUND, USEFUL FOR PANCREATIC LIPASE INHIBITION AND THE PROCESS FOR ISOLATION THEREOF

(75) Inventors: Avinash Prahalad Sattur, Karnataka (IN); Naveen Babu Kilaru, Karnataka (IN); Lingamallu Jagan Mohan Rao, Karnataka (IN); Naikanakatte Ganesh Karanth, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 65 days.

(21) Appl. No.: 12/091,550

(22) PCT Filed: Oct. 23, 2006

(86) PCT No.: PCT/IB2006/002964

§ 371 (c)(1),
(2), (4) Date: Oct. 9, 2008

(87) PCT Pub. No.: WO2007/049119

PCT Pub. Date: May 3, 2007

(65) Prior Publication Data

US 2009/0163443 A1     Jun. 25, 2009

(30) Foreign Application Priority Data

Oct. 25, 2005  (IN) .................. 1896/DEL/2005

(51) Int. Cl.
*A61K 31/495*   (2006.01)
(52) U.S. Cl. ...................... 514/249; 544/354
(58) Field of Classification Search ........ 514/249; 544/354
See application file for complete search history.

(56) References Cited

FOREIGN PATENT DOCUMENTS

WO     00/40569 A1     7/2000

OTHER PUBLICATIONS

E.K. Weibel, et al; "Lipstatin, An Inhibitor of Pancreatic Lipase, Produced By *Streptomyces Toxytricini* I. Producing Organism, Fermentation, Isolation and Biological Activity", The Journal of Antibiotics, Japan Antibiotics Research Association, Tokyo, JP, vol. 40, No. 8, Aug. 1987, pp. 1081-1085; XP001027737.

*Primary Examiner*—James O Wilson
*Assistant Examiner*—Douglas M Willis
(74) *Attorney, Agent, or Firm*—Ladas & Parry LLP

(57) ABSTRACT

The present invention relates to a novel, Nonadeca-6-enoic acid-3-(hexadecyloxy-hydroxy-thiophosphoryloxy)-quinoxalin-2-yl ester designated as streptolipin, useful for pancreatic lipase inhibition, isolated from the culture of *Streptomyces vayuensis* strain N2 having molecular formula (1) and a process for the preparation thereof.

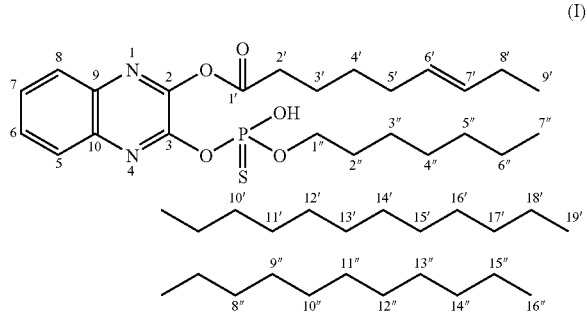

2 Claims, No Drawings

COMPOUND, USEFUL FOR PANCREATIC LIPASE INHIBITION AND THE PROCESS FOR ISOLATION THEREOF

FIELD OF INVENTION

The present invention relates to the field of treatment of various diseases caused by pancreatic lipase activity. Particularly the present invention relates to isolation of a new compound useful for inhibiting pancreatic lipase activity. More particularly the present invention relates to a novel compound, Nonadeca-6-enoic acid-3-(hexadecyloxy-hydroxy-thiophosphoryloxy)quinoxalin-2-yl ester, designated as streptolipin, useful for pancreatic lipase inhibition, isolated from the culture of Streptomyces vayuensis strain N 2 having a molecular formula C.sub.43H.sub.73 N sub 2 PS O.sub.5 and a process for the preparation thereof. The present invention also relates to a method of inhibiting lipase activity.

BACKGROUND AND PRIOR ART REFERENCES

Lipase catalyzes the hydrolysis of triglycerides to fatty acids and glycerol. Pancreatic lipase is the principle enzyme for digestion of dietary triglycerides and there fore pays a key role in absorption of fat from the small intestine. In conjunction with cofactors co lipase, pancreatic lipase hydrolyzes medium and long chain triglycerides to oil water interface to fatty acids and 2 mono glycerides. These fatty acids get accumulated in the body as a reserve source of energy. Excess accumulation of fat in the body leads to obesity. Inhibitor against this enzyme can be used as an antiobesity drug.

M. K. Meir, J. Tricari and Sullivan. Studies on the antiobesity activity of tetrahydrolipstatin, A potent and selective inhibitor of pancreatic lipase. International Journal of Obesity. (1987) 11, 35-42.

Obesity and hyperlipidaemia are medical conditions associated with a series of risk factors such as insulin resistance, impaired glucose tolerance, hypertension, hart diseases and stroke leading to an increased rate of mortality. Inhibitors against these enzymes thus have a potential application in medical sector.

Comparison of galenic formulations of orlistat (Tetrahydrolipstatin) A pharmacological approach. Drug Invest: 5(1): 44-50 (1993)

Weibel et al (1987) have reported that therapeutically active compound such as lipstatin as pancreatic lipase inhibitor (Weibel E K, Hadvary P, Hochuli E, Kupfer E and Lengsfeld H. The Journal of Antibiotics XL (1987) 1081-10191.

Panclicins, as novel pancreatic lipase inhibitors have been reported. Masae Mutoh, Naoki Nakada, Shoka Matsukuma, Shoichi Ohshima, Kiyoshi Yoshinari, Junko Watanabe and Mikio Arisawa. The Journal of Antibiotics vol 47, 1369-1375. Wherein the authors have discussed the use of various pancreatic lipase inhibitors in treatment of obesity.

OBJECTS OF THE PRESENT INVENTION

The main object of the present invention is to provide A novel compound, Nonadeca-6-enoic acid-3-(hexadecyloxy-hydroxy-thiophosphoryloxy)-quinoxalin-2-yl ester, designated as streptolipin, useful for pancreatic lipase inhibition, isolated from the culture of Streptomyces vayuensis strain $N_2$ having molecular formula $C_{43}H_{73}N_2 PSO_5$ and structural formula as hereunder:

Formula 1

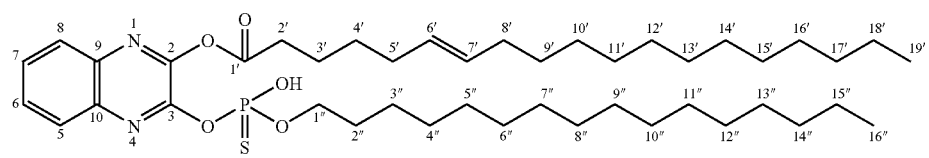

An another object of the present invention is to provide a process for the isolation of said compound.

Yet another object of the present invention is to provide a method of treatment to inhibit lipase enzyme and for the prevention of obesity and treatment of disorders of the central nervous system; damage to the central nervous system; cardiovascular disorders; gastrointestinal disorders; diabetes, sleep apnea.

SUMMARY OF THE INVENTION

To meet the above objectives, the present invention provides a novel compound, Nonadeca-6-enoic acid-3-(hexadecyloxy-hydroxy-thiophosphoryloxy)-quinoxalin-2-yl ester, designated as streptolipin, useful for pancreatic lipase inhibition, isolated from the culture of Streptomyces vayuensis strain $N_2$ having molecular formula C.sub.43H.sub.73 N sub 2 PS O.sub.5. The present invention also provides a process for the isolation/preparation of said compound from Streptomyces sp and a method treatment in inhibiting lipase inhibitor, for the treatment of obesity and treatment of disorders of the central nervous system; damage to the central nervous system; cardiovascular disorders; gastrointestinal disorders; diabetes, sleep apnea.

STATEMENT OF THE INVENTION

Accordingly, the present invention provides a novel compound, Nonadeca-6-enoic acid-3-(hexadecyloxy-hydroxy-thiophosphoryloxy)-quinoxalin-2-yl ester, designated as streptolipin, useful for pancreatic lipase inhibition, isolated from the culture of Streptomyces vayuensis strain $N_2$, said compound having a molecular formula $C_{43}H_{73}N_2 PSO_5$ and the structural formula as hereunder:

Formula 1

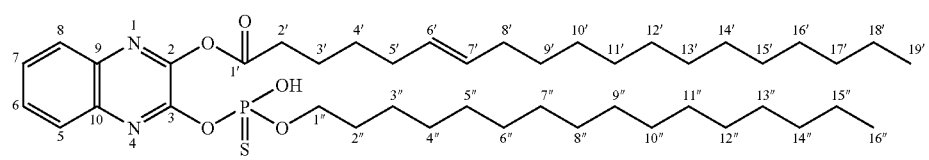

wherein the said compound having a basic skeleton of quinoxaline moiety having substituents carbonyl ester and phosphotidyl groups. Said compound is soluble in an organic solvent selected from the group consisting of chloroform, acetone and dimethyl sulphoxide. The detailed solubility character of the said compound is as hereunder:

| SOLVENTS | SOLUBILITY RESPONSE |
|---|---|
| Acetone | Soluble |
| Chloroform | Soluble |
| Dimethyl sulphoxide | Soluble |
| Ethyl acetate | Sparingly soluble |
| Methanol | Sparingly soluble |
| Hexane | Sparingly soluble |
| Ethanol | Sparingly soluble |
| Diethyl ether | Sparingly soluble |
| Acetonitrile | Sparingly soluble |
| Phosphate buffer (pH 7.4-8.0) | Insoluble |
| acetate buffer (pH 5.0, 6.0) | Insoluble |
| tris buffer (pH 8.0, 9.0) | Insoluble |
| 5% sodium hydroxide | Insoluble |
| 5% acetic acid | Insoluble |
| 5% sodium bicarbonate | Insoluble |
| water | Insoluble | wherein the said compound is insoluble in phosphate buffer (pH 7.4, 8.0), acetate buffer (pH 5.0, 6.0), tris buffer (pH 8.0, 9.0), 5% sodium hydroxide, 5% acetic acid, 5% sodium bicarbona and the said compound having the physical characteristics as given below:

Lipase inhibition activity: $IC_{50}$ value of the compound against purified pancreatic lipase inhibitory activity is 49 nM; Off white solid. Melting Point: 184.degree. C. λ max (chloroform): 210, 260; IR: 1434, 1312, 1046, 954, 761 for quinoxaline, 3436, 2913, 1771, 1714, 1659, 1236, 667 cm$^{-1}$. Molecular formula: $C_{43}H_{73}N_2PSO_5$ EI-MS m/z: 761 ($M^+$), 763 $[M+2]^+$, [M−X]+468.4, [M−Y]+427, [M−Z]+584.4, [M-$C_{18}H_{33}$] 514.4, [M-$C_{12}H_{24}$] 595.4, $PO_3S$—$C_{16}H_{34}$ 337[Y], $O_2C_{19}H_{35}$ 295 [X], $C_{13}H_{25}$ 181[Z], $C_{15}H_{15}O_2N_2$ 255, $PO_3HS$ 112, $CH_2$—$(CH_2)_{14}$—$CH_3$ 225, $C_9H_4N_2$ 128. $^1H$ NMR (500 MHz, $CDCl_3$) δ: 7.82-8.15 (4H, m, Ar—H—) 0.87-0.93 (3H, t, $CH_3$) 1.26-1.38 (2H, m, CH sub 2) 1.6-1.7 (1H, t, =$CH_2$) 5.86 (1H, dd, C—CH=C) 2.04-2.12 (2H, t, O=C—CH sub 2) 2.36-2.39 (2H, t, O—CH sub 2), 5.37 (1H, s, —OH), 1.92-1.96 (2H, q, $CH_2$—$CH_2$). $^{13}C$ NMR spectra (δ ppm): quinoxaline-N=$C_2$—O 171.19, quinoxaline-N=C—OP 155.3, quanoxaline-$CH_2$ $CH_2$=$CH_2$ 130.41, quanoxaline-$CH_2$=$CH_2$—$CH_2$— 128.422, quanoxaline-$CH_2$—$CH_2$=$CH_2$— 128.28, quanoxaline-$CH_2CH_2$—$CH_2$— 130.12, quanoxaline-$CH_2$—$CH_2$—NH— 138.84, quanoxaline-$CH_2$—$CH_2$—NH— 140.268, CH=CH 147.833, CH=CH 122.425, O—C=O 179.7, —$CH_3$ 14.4, —$CH_2$ 23.03, =$CH_2$ 32.3, C—CH=C 39.6, CH=CH—C 30.6, O—$CH_2$— 24.32, —$CH_2$—C 29.45.

Yet another embodiment of the present invention is to provide a pharmaceutical composition, useful for effecting lipase inhibition in subjects mammals, comprising the said novel compound optionally along with pharmaceutically accepted salts, diluents and other excipients selected from the group consisting of carriers, colorants, flow modifiers and stabilizers. The said pharmaceutical composition is useful particularly for prevention of obesity and treatment of disorders of the central nervous system; damage to the central nervous system; cardiovascular disorders; gastrointestinal disorders; diabetes and sleep apnea. The said pharmaceutical composition is used in the form of oral, parental, buccal and ocular administration.

Yet another objective of the present invention is to provide a process for the preparation a novel compound, Nonadeca-6-enoic acid-3-(hexadecyloxy-hydroxy-thiophosphoryloxy)-quinoxalin-2-yl ester designated as streptolipin, useful for pancreatic lipase inhibition, which comprises the steps of:

(a) isolating by a known method *Streptomyces vayuensis* strain $N_2$ having MTCC No. 5219 from rich manure soil sample;

(b) propagating by a known method the strain obtained in step (a) in order to obtain to obtain fermented broth;

(c) separating the biomass obtained in step (b) by centrifugation and treating the fermented broth with an organic solvent for about two hours to obtain an organic solvent extract by a known method;

(d) separating the organic solvent extract of step (c) by a known method;

(e) drying the organic solvent extract obtained in step (d) over anhydrous sodium sulfate followed by concentrating under reduced pressure in order to obtain the said compound in form of a solid;

(f) loading the solid, dissolved in chloroform, of the compound obtained in step (e) on to silica gel (# 60-120) column chromatography followed by elution with solvent mixture of hexane and ethylacetate at the ratio of about 9:1;

(g) recovering from the step (f) the colorless fraction in hexane:ethyl acetate (9:1) followed by concentration under reduced pressure in order to obtain the compound concentrated form;

(h) chromatographing the concentrated compound obtained in step (g) on sephadex LH-20 with methanol in order to check for the active fraction on TLC (thin layer chromatography) followed by purification on preparative TLC using benzene:ethyl acetate (7:3) and benzene:methanol (9:1) in order to obtain silica gel having the said compound;

(i) extracting the silica gel obtained in step (i) with diethyl ether followed by filtration in order to obtain the compound in form of an off white solid filtrate;

(j) concentrating the filtrate obtained in step (i) under reduced pressure in order to obtain the compound having a molecular formula $C_{43}H_{73}N_2PSO_5$ of the following structure:

Formula 1

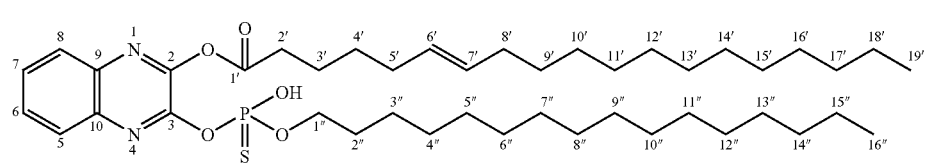

wherein the said compound has a basic skeleton of quinoxaline moiety having two substituents namely phosphotidyl and carbonyl ester groups; AND (k) drying the biomass obtained in step (b) at a temperature of about 40. degree. C followed by extraction with ethyl acetate and further purification of the compound by steps (e)-(j) in order to prepare at large scale the compound having a molecular formula $C_{43}H_{73}N_2PSO_5$ of the following structure:

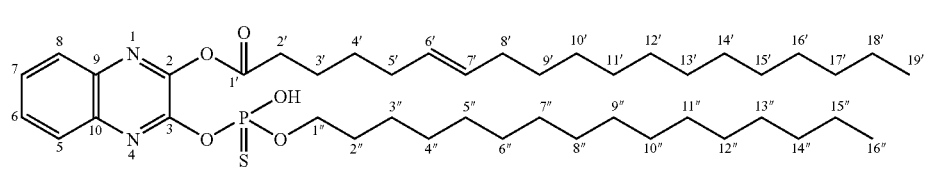

Formula 1 wherein the said compound has a basic skeleton of quinoxaline moiety having two substituents namely phosphotidyl and carbonyl ester groups. The organic solvent used in step (c) is selected from the group consisting of acetone, dichloro methane, methyl isobutyl ketone, chloroform, ethyl acetate and preferably ethylacetate.

DETAILED DESCRIPTION OF THE INVENTION

The following examples are given by a way of illustrating the present invention and therefore shall not be construed to limit scope of the present invention.

The Isolation of the *Streptomyces vayuensis* Strain $N_2$

Fermentation

Example-1

Seed Culture

Strain $N_2$ is propagated on Glycerol Aspargine Agar slant composed of glycerol 1%, L-aspargine 0.1%, $K_2HPO_4$ 0.1% and trace salt solution 0.1%. After incubation for 7 days at 30.degree. C., a portion of the mature agar slant is inoculated into 100 ml of a seed liquid medium of the same medium composition in a 500-ml Erlenmeyer flask and incubated at 30.degree. C. on a rotary shaker at 250 rpm.

Example-2

Flask Fermentation

A 10-ml of the seed culture is transferred into 500-ml Erlenmeyer flasks each containing 90 ml of soybean meal 1 g, dextrose 2 g, corn steep liquor 0.5 g, calcium carbonate 0.5 g for 100 ml. The inoculated flasks are incubated for 7 days at 30.degree. C.

Example-3

Isolation and Purification

Isolating the strain $N_2$ of *Streptomyces* sp from manure rich soil and propagating the strain obtained from step on a Glycerol Aspargine Agar medium and incubating for 7 days at 30.degree. C. Inoculating with a slant of step into seed liquid medium contained in Erlenmeyer flask, incubating the liquid medium in Erlenmeyer flask at 28.degree. C. on a rotary shaker at 250 rpm to obtain the seed culture; transferring the culture of step into Erlenmeyer flasks containing soya bean meal, soluble starch, dextrose, corn steep liquor, calcium carbonate and incubated for 7 days at 30.degree. C. to obtain fermented broth. Biomass was separated by centrifugation and treating the fermented broth with an organic solvent for two hours to obtain an organic solvent extract; separating the organic solvent extract of step. the organic layer was separated by separating funnel; drying the organic layer of step over anhydrous sodium sulfate and concentrating under reduced pressure to obtain a solid; the compound is loaded on to silica gel (#60-120) column chromatography and eluted with hexane, hexane:ethylacetate (9:1) where it elutes as a colorless fraction in hexane ethylacetate (9:1), concentrated under reduced pressure chromatographed on sephadex LH-20 with methanol, checked for the active fraction on TLC and further purified on preparative TLC using benzene:ethyl acetate (7:3) and benzene:methanol (9:1). The silica gel was extracted with diethyl ether to obtain an off white solid. The silica gel was extracted with diethyl ether to obtain an off white solid. The biomass was dried at 40. degree. C and the dried biomass was extracted with ethyl acetate and further purification of the compound was carried by steps g, h, i, j, k which were carried out for broth extraction.

The composition of glycerol asparagine media: (g/) Asparagine 1, glycerol 10, K2HPO4 1; 1 ml trace salt solution (from stock of 1 Litre) CuSO4 64 mg, FeSO4 11 mg, MnCl2 79 mg, ZnSO4 15 mg, PH 7 and The seed liquid medium composition (g/L): glucose 50, yeast extract 50 NaCl 2.5, K2HPO4 0.5, ZnSO4 0.1, CaCO3 0.4, PH 7 The other ingredients occurring elsewhere in the patent Starch is 10 g/l, soybean meal 50 g/L.

For separating the biomass the centrifugation speed used is 5000 rpm for 20 minutes.

Example-4

Physico-Chemical Properties

The compound is off white solid. It is soluble in acetone, chloroform and dimethyl sulphoxide, slightly soluble in ethylacetate, methanol, acetonitrile, diethyl ether, but insoluble in water, phosphate buffer (pH 7.4, 8.0), acetate buffer (pH 5.0, 6.0), tris buffer (pH 8.0, 9.0), 5% sodium hydroxide, 5% acetic acid, 5% sodium bicarbonate. The EI-MS spectra of the compound showed the molecular ions at m/z 761.

Example-5

Compositions and Methods

The novel compounds of the invention can be used in a variety of pharmaceutical dosage forms. Thus, oral, buccal, ocular and other forms can be used. When such forms are formulated they will include pharmaceutically acceptable excipients such as colorants, carriers, perfumes, stabilizers, flow modifiers and the like in suitable amounts (i.e., from 0.001 to 0.99 wt %).

The compound of the invention is useful in methods of inhibiting the effects of pancreatic lipase. The compound is also used to treat a host, preferable a mammal, which is suffering from a disorder associated with a metabolism of disorders of the central nervous system; damage to the central nervous system; cardiovascular disorders; gastrointestinal disorders; diabetes, sleep apnea.

Example-6

A biologically pure culture of *Streptomyces* sp $N_2$, from which the compound of investigation is derived, has been deposited with the Microbial Type Culture Collection (MTCC), The Institute of Microbial Technology (IMTECH), India. The assigned MTCC Number is 5219

Taxonomy

Morphology The actinomycetes mycelium on different ISP medium agar had abundant spores more than 50, spiral, spore chains are long, non motile gray colored spores when matured.

Cultural and Physiological Characteristics

The growth characteristics of $N_2$ on different media is given in table 2. The aerial mycelium at maturity formed long chains of spores of gray color, which are spiral, with warty surface and are non motile. Good growth on most of the media. Optimum temperature is between 10 to 45° C. There is no distinctive substrate mycelial pigments, no pigmentation of substrate mycelium, no production of diffusible pigments, no sensitivity of substrate pigment to pH, no sensitivity of diffusible pigment to pH, melanin production is negative. There are no sporulation on substrate mycelium, no sclerotia formation, and no fragmentation of mycelium. It doesn't show any antagonist activity against any organism. It degrades guanine, hypoxanthine, adenine, Xanthine, starch, casein, urea, gelatin. It is not resistant to all antibiotics, it grows at pH between 5 and 13. The sodium chloride tolerance is up to 5%. diffusible pigment is not produced. The color of the colonies is medium dependent (Table-2). Diagnostic amino acid of petidoglycan is meso-diaminopimelic acid. Whole cell hydrolysates contain glucose and small quantity of xylose, galactose and arabinose. The phosphotidylethanolamine is the diagnostic phospholipid. Predominant fatty acids are anreso-15:0, iso-16:0 and cyclo 17:0.

Table 1: Table 1 illustrates the list of culture characteristics.
Table 2: Table 2 illustrates the Cultural characteristics of isolate $N_2$ on different media.
Table 3: Table 3 illustrates the production of acid and gas against culture on various substrates.
Table 4: Table 4 illustrates the growth on the sole carbon source (1.0% w/v)
Table 5: Table 5 illustrates the growth on sole nitrogen source (0.1% w/v)
Table 6: Table 6 illustrates the growth in the presence Sodium chloride (% w/v)
Table 7: Table 7 illustrates the growth at different pH
Table 8: Table 8 illustrates the growth at different temperature
Table 9: Table 9 illustrates the degradation characteristics
Table 10: Table 10 illustrates the antimicrobial activity
Table 11: Table 11 illustrates the production of acid
Table 12: Table 12 illustrates the comparative studies of $N_2$ with standard cultures
Table 13: Table 13 illustrates the cultural characteristics on different media In Table 2 illustrating the growth on yeast extract and malt extract is good, colour of the aerial mycelium is blackish gray and substrate mycelium is black. Oat meal the growth is good, aerial mycelium is gray, substrate mycelium is dark brown. Inorganic salt starch agar, the growth is good, grayish white aerial mycelium, reddish brown substrate mycelium. The growth on glycerol aspargine agar, the growth is good, the colour of aerial mycelium is grayish white, substrate mycelium is blackish. Peptone yeast extract iron agar, the is moderate, colour of aerial mycelium is grayish black, gray colour substrate mycelium.

Table 5 illustrating the growth of *Streptomyces* sp $N_2$ in the presence of various carbon and nitrogen sources. It had very good growth on DL-α-amino butyric acid, potassium nitrate, L-cysteine, L-threonine, L-serine, L-lysine, L-methionine, L-histidine, L-hydroxy proline, tryptophan, glutamic acid, tyrosine, ornithine mono hydrochloride, glycine, L-leucine, dopa, alanine, L-arabinose, sorbitol, starch, D-xylose, meso-inositol, mannitol, D-fructose, D-glucose, L-rhamnosse, maltose, D-mannose, D-lactose, trehalose, D-melibiose, D-galactose, cellobiose, moderate growth on L-valine, cellulose, sodium acetate, sodium citrate, xylitol, sodium pyruvate, sodium propionate and no growth on sodium malonate, insulin, sucrose aspartic acid.

Taxonomic Position

The strain Actinomycete $N_2$ is isolated from rich manure soil sample from local region. The characteristics indicated that the strain belongs to *Streptomyces* group. According to the descriptions of Bergeys Manual of Bacteriology the strain is related to *Streptomyces* sp.

The taxonomic relationships between the strains and five other cultures *Streptomyces erumpens, Streptomyces albduncus, Streptomyces olivvaceiscleroticus, Streptomyces viridodiastaticus, Streptomyces viridiviolaceus* that did not give the bioactive molecules during screening are compared and given in Table 2.

Comparative Study:

In Table 11 illustrating Comparison between the strains $N_2$ and five other related species which did not give the compound I. The spore surface of $N_2$ was warty surface as the NRRL cultures of the above five strains are smooth surface and it also differs with the standard strains in physiological and biochemical.

Example-7

The activity of pancreatic lipase against P-nitrophenyl butyrate was measured in 0.15 M of sodium chloride, 0.1M sodium phosphate buffer pH 7.4 at 25.degree.C. in a glass cuvette with a 1-cm light path. The substrate concentration 0.05 mM (from 10 mM stock solution of acetonitrile). The total volume three ml and the assay mixture enzyme concentration was x ml. The release of P-nitrophenol was monitored using spectrophotometer at 400 nm, and the reaction rate is determined from the slope of the straight-line portion of the curve. The activity was calculated from the initial rate of the reaction after the spontaneous hydrolysis of the substrate had been subtracted.

Results

The inhibitor compound having molecular formula C.sub.43H.sub.73 N sub 2 PS O.sub.5 is discovered in the fermented broth of a species of Streptomyces sp $N_2$. The compound is successfully purified to homogeneity. The $IC_{50}$ value of the compound against purified pancreatic lipase inhibitory activity is determined to be 349 nM.

Novelty

The compound, Nonadeca-6-enoic acid-3-(hexadecyloxy-hydroxy-thiophosphoryloxy)-quinoxalin-2-yl ester, designated as streptolipin, useful for pancreatic lipase inhibition, isolated from the culture of *Streptomyces vayuensis* strain $N_2$, per se is novel. The process is novel because the culture '*Streptomyces vayuensis* strain $N_2$' and the product Nonadeca-6-enoic acid-3-(hexadecyloxy-hydroxy-thiophosphoryloxy)-quinoxalin-2-yl ester obtained in the process are novel.

TABLE 1

Culture characters:

| S. No | Morphological and pigmentation | Observation |
|---|---|---|
| 1 | Spore chain morphology | Spirales |
| 2 | Spore chain ornamentation | Warty |
| 3 | Colour of aerial spore mass | Gray |
| 4 | No distinctive substrate mycelial pigments | Nil |
| 5 | Pigmentation of substrate mycelium | Nil |
| 6 | Production of diffusible pigments | Nil |
| 7 | Sensitivity of substrate pigment to pH | Nil |
| 8 | Sensitivity of diffusible pigment to pH | Nil |
| 9 | Melanin production on peptone/yeast/iron agar | −Ve |
| 10 | Melanin production on tyrosine agar | −Ve |
| 11 | Fragmentation of mycelium | Nil |
| 12 | Sclerotia formation | Nil |
| 13 | Sporulation on substrate mycelium | Nil |

TABLE 2

Cultural characteristics of isolate $N_2$ on different media:

| S. No | Media | Growth | Aerial mycelium | Substrate mycelium | Soluble pigment |
|---|---|---|---|---|---|
| 1 | Yeast extract Malt extract agar | Good | Blackish gray | Black | Nil |
| 2 | Oat meal agar | Good | White | Dark brown | Nil |
| 3 | Inorganic salt and starch agar | Good | Grayish white | Reddish brown | Nil |
| 4 | Glycerol aspargine agar | Good | Grayish white | Blackish brown | Nil |
| 5 | Peptone yeast extract iron agar | Moderate | Grayish black | Gray | Nil |
| 6 | Tyrosine agar | Good | Grayish black | Gray | Nil |
| 7 | Starch casein agar | Good | Gray | White | Nil |
| 8 | Potato dextrose agar | Good | Grayish white | Dirty green | Nil |
| 9 | Nutrient agar | Moderate | White | Colorless | Nil |
| 10 | Glucose aspargine agar | Good | Grayish black | Colorless | Nil |
| 11 | Bennets agar | Moderate | Colorless | Colorless | Nil |
| 12 | Czapek dox agar | Good | Gray | White | Nil |

TABLE 3

Production of Acid and Gas:

| S. No | Carbon source | Acid | Gas |
|---|---|---|---|
| 1 | Starch | + | − |
| 2 | Melibiose | + | − |
| 3 | Inositol | + | − |
| 4 | Arabinose | + | − |
| 5 | Mannose | − | − |
| 6 | Xylose | − | − |
| 7 | Mannitol | − | − |
| 8 | Lactose | + | − |
| 9 | Tyrosine | + | − |
| 10 | Rhaminose | + | − |
| 11 | Fructose | + | − |
| 12 | Glucose | + | − |
| 13 | Galactose | + | − |
| 14 | Maltose | + | − |
| 15 | Inulin | + | − |
| 16 | Xylitol | + | − |
| 17 | Sodium acetate | − | − |
| 18 | Sucrose | − | − |
| 19 | Sodium citrate | − | − |
| 20 | Cellulose | + | − |

TABLE 4

Growth on the sole carbon source (1.0% w/v)

| S. No | Carbon source | Observation |
|---|---|---|
| 1 | L-Arabinose | ++ |
| 2 | Cellulose | + |
| 3 | Sucrose | − |
| 4 | Starch | ++ |
| 5 | Sorbitol | ++ |
| 6 | D-Xylose | ++ |
| 7 | meso-Inositol | ++ |
| 8 | Mannitol | ++ |
| 9 | D-Fructose | ++ |
| 10 | D-Glucose | ++ |
| 11 | L-Rhamnose | ++ |
| 12 | Raffinose | + |
| 13 | Maltose | ++ |
| 14 | D-Mannose | ++ |

TABLE 4-continued

Growth on the sole carbon source (1.0% w/v)

| S. No | Carbon source | Observation |
|---|---|---|
| 15 | D-Lactose | ++ |
| 16 | Inulin | − |
| 17 | Trehalose | ++ |
| 18 | D-Melibiose | ++ |
| 19 | Dextran | ++ |
| 20 | D-Galactose | ++ |
| 21 | Cellobiose | ++ |
| 22 | Xylitol | + |
| 23 | Sodium acetate (0.1% w/v) | + |
| 24 | Sodium citrate (0.1% w/v) | + |
| 25 | Sodium malonate (0/1% w/v) | − |
| 26 | Sodium propionate (0.1% w/v) | + |
| 27 | Sodium pyruvate (0.1% w/v) | + |

TABLE 5

Growth on sole nitrogen source (0.1% w/v)

| S. No | Nitrogen source | Observation |
|---|---|---|
| 1 | DL-α-Amino-n-butyric acid | ++ |
| 2 | Potassium nitrate | ++ |
| 3 | L-Cysteine | ++ |
| 4 | L-Valine | + |
| 5 | L-Threonine | ++ |
| 6 | L-Serine | ++ |
| 7 | L-Phenylalanine | + |
| 8 | L-Lysine | ++ |
| 9 | L-Methiionine | ++ |
| 10 | L-Histidine | ++ |
| 11 | L-Arginine | + |
| 12 | L-Hydroxy proline | ++ |
| 13 | Tryptophan | ++ |
| 14 | Glutamic acid | ++ |
| 15 | Tyrosine | ++ |
| 16 | Ornithine mono HCl | ++ |
| 17 | Glycine | ++ |
| 18 | L-Leucine | ++ |
| 19 | Aspartic acid | − |
| 20 | Dopa | ++ |
| 21 | Alanine | ++ |

TABLE 6

Growth in the presence Sodium chloride (% w/v)

| S. No | Sodium chloride (% w/v) | Observation |
|---|---|---|
| 1 | Control | ++ |
| 2 | 1 | ++ |
| 3 | 3 | ++ |
| 4 | 5 | ++ |
| 5 | 7 | − |
| 6 | 9 | − |
| 7 | 11 | − |
| 8 | 13 | − |

TABLE 7

Growth at different pH

| S. No | pH | Observation |
|---|---|---|
| 1 | 2 | − |
| 2 | 5 | ++ |
| 3 | 7 | ++ |
| 4 | 9 | ++ |
| 5 | 11 | ++ |
| 6 | 13 | ++ |

TABLE 8

Growth at different temperature ° C.

| S. No | Temperature ° C. | Observation |
|---|---|---|
| 1 | 4 | − |
| 2 | 10 | ++ |
| 3 | 20 | ++ |
| 4 | 28 | ++ |
| 5 | 37 | ++ |
| 6 | 45 | + |

TABLE 9

Degradation characteristics

| S. No | Degradation of | Observation |
|---|---|---|
| 1 | Hpoxanthine | + |
| 2 | Guanine | + |
| 3 | L-Tyrosine | − |
| 4 | Trptophan | − |
| 5 | Adenine | + |
| 6 | Xanthine | + |
| 7 | Tween 20 | − |
| 8 | Tween 40 | − |
| 9 | Tween 60 | − |
| 10 | Tween 80 | − |
| 11 | Starch | + |
| 12 | Xylan | − |
| 13 | Casein | + |
| 14 | Urea | + |
| 15 | Allantoin | − |
| 16 | Gelatin | + |
| 17 | Aesculin | − |
| 18 | Arbutin | − |

TABLE 10

Antimicrobial activity

| S. No | Antimicrobial activity | Observation |
|---|---|---|
| 1 | *Bacillus subtilis* NCIB 3610 | −Ve |
| 2 | *Pseudomonas fluorescens* NCIB 9046 | −Ve |
| 3 | *Escherichia coli* NCIB 9132 | −Ve |
| 4 | *Micrococcus luteus* NCIB 196 | −Ve |
| 5 | *Candida albicans* CBS 562 | −Ve |
| 6 | *Saccharomyces cerevisiaae* CBS 1171 | −Ve |
| 7 | *Streptomyces murinus* ISP 5091 | −Ve |
| 8 | *Aspergillus niger* LIV 131 | −Ve |
| 9 | Nitrate reduction | −Ve |
| 10 | Hydrogen sulphide production | −Ve |
| 11 | Milk coagulation and peptonization | −Ve |

TABLE 11

Production of acid

| Carbon source | $N_2$ | Streptomyces erumpens | Streptomyces albduncus | Streptomyces olivvaceiscleroticus | Streptomyces viridodiastaticus | Streptomyces viridiviolaceus |
|---|---|---|---|---|---|---|
| Starch | + | + | | + | + | + |
| Melibiose | + | − | + | + | − | + |
| Inositol | + | + | | + | + | + |
| Arabinose | + | − | − | − | − | + |
| Mannose | − | − | − | − | − | + |
| Xylose | − | − | − | − | − | + |
| Mannitol | − | + | + | − | − | + |
| Lactose | + | + | − | + | − | + |
| Tyrosine | + | + | + | + | + | + |
| Rhaminose | + | − | − | − | + | − |
| Fructose | + | − | − | − | − | + |
| Glucose | + | − | − | − | + | − |
| Galactose | + | − | − | − | − | + |
| Maltose | + | + | + | + | + | + |
| Inulin | + | + | + | + | + | + |
| Xylitol | + | + | − | + | + | + |
| Sodium acetate | − | + | − | + | + | − |
| Sucrose | − | + | + | − | + | + |
| Sodium citrate | − | + | + | + | + | − |
| Cellulose | + | + | − | + | + | + |

TABLE 12

Comparative studies of $N_2$ with standard cultures:

| Characters/Tests | $N_2$ | Streptomyces erumpens | Streptomyces albduncus | Streptomyces olivvaceiscleroticus | Streptomyces viridodiastaticus | Streptomyces viridiviolaceus |
|---|---|---|---|---|---|---|
| Morphological and pigmentation | | | | | | |
| Spore chain morphology | Spirales | Spirales | Retinaculiaperti | Spirales | Retinaculiaperti | Retinaculiaperti |
| Spore chain ornamentation | Warty | Smooth | Spiny | Smooth | Spiny | Spiny |
| Colour of aerial spore mass | Gray | Gray | Gray | Gray | Gray | Gray |
| No distinctive substrate mycelial pigments | Nil | Nil | Nil | Nil | Nil | Nil |
| Pigmentation of substrate mycelium | Nil | Nil | Yellow to yellowish brown | Grayish yellow to olive brown | Yellowish brown to olive brown | Reddish brown |
| Production of diffusible pigments | Nil | Nil | Nil | Nil | Nil | Orange or Red |
| Sensitivity of substrate pigment to pH | Nil | Nil | Nil | Nil | Nil | +Ve |
| Sensitivity of diffusible pigment to pH | Nil | Nil | Nil | Nil | Nil | +Ve |
| Melanin production on peptone/yeast/iron agar | −Ve | −Ve | −Ve | −Ve | −Ve | −Ve |
| Melanin production on tyrosine agar | −Ve | −Ve | −Ve | −Ve | −Ve | −Ve |
| Fragmentation of mycelium | Nil | Nil | Nil | Nil | Nil | Nil |
| Sclerotia formation | Nil | Nil | Nil | +ve | Nil | Nil |
| Sporulation on substrate mycelium | Nil | Nil | Nil | Nil | Nil | Nil |
| Antimicrobial activity against | | | | | | |
| Bacillus subtilis NCIB 3610 | −Ve | −Ve | −Ve | −Ve | −Ve | −Ve |
| Pseudomonas fluorescens NCIB 9046 | −Ve | −Ve | −Ve | −Ve | −Ve | −Ve |
| Escherichia coli NCIB 9132 | −Ve | −Ve | −Ve | −Ve | −Ve | −Ve |

TABLE 12-continued

Comparative studies of $N_2$ with standard cultures:

| Characters/Tests | $N_2$ | Streptomyces erumpens | Streptomyces albduncus | Streptomyces olivvaceiscleroticus | Streptomyces viridodiastaticus | Streptomyces viridiviolaceus |
|---|---|---|---|---|---|---|
| Micrococcus luteus NCIB 196 | −Ve | −Ve | −Ve | −Ve | −Ve | −Ve |
| Candida albicans CBS 562 | −Ve | −Ve | −Ve | −Ve | −Ve | −Ve |
| Saccharomyces cerevisiaae CBS 1171 | −Ve | −Ve | −Ve | −Ve | −Ve | −Ve |
| Streptomyces murinus ISP 5091 | −Ve | −Ve | −Ve | −Ve | −Ve | −Ve |
| Aspergillus niger LIV 131 | −Ve | Ve | +Ve | +Ve | −Ve | +Ve |
| Nitrate reduction Hydrogen sulphide production | −Ve | −Ve | −Ve | −Ve | −Ve | −Ve |
| Milk coagulation and peptonization | −Ve | −Ve | −Ve | −Ve | −Ve | +Ve |

Degradation of

| | | | | | | |
|---|---|---|---|---|---|---|
| Hpoxanthine | + | − | − | − | + | + |
| Guanine | + | − | − | − | − | + |
| L-Tyrosine | − | − | − | − | + | − |
| Trptophan | − | − | − | − | − | + |
| Adenine | + | − | − | − | + | + |
| Xanthine | + | − | − | − | + | − |
| Tween 20 | − | − | + | + | − | − |
| Tween 40 | − | − | − | − | − | − |
| Tween 60 | − | − | − | − | − | − |
| Tween 80 | − | − | − | − | − | − |
| Starch | + | + | + | + | + | + |
| Xylan | − | − | + | − | − | + |
| Casein | + | + | + | + | + | + |
| Urea | + | − | − | − | − | − |
| Allantoin | − | − | − | − | − | + |
| Gelatin | + | − | − | − | − | − |
| Aesculin | − | − | − | − | − | − |
| Arbutin | − | − | − | − | − | − |

Resistance to antibiotics (μg ml)

| | | | | | | |
|---|---|---|---|---|---|---|
| Gentamicin (100) | −Ve | −Ve | −Ve | −Ve | −Ve | −Ve |
| Neomycin (50) | −Ve | −Ve | −Ve | −Ve | −Ve | −Ve |
| Streptomycin (100) | −Ve | −Ve | +Ve | +Ve | −Ve | −Ve |
| Tobramycin (50) | −Ve | −Ve | −Ve | −Ve | −Ve | −Ve |
| Rifampicin (50) | −Ve | −Ve | −Ve | −Ve | −Ve | −Ve |
| Cephaloridine (100) | −Ve | −Ve | −Ve | −Ve | −Ve | −Ve |
| Vancomycin (50) | +Ve | −Ve | −Ve | −Ve | −Ve | −Ve |
| Dimethylchlortetracycline (500) | −Ve | −Ve | −Ve | −Ve | −Ve | −Ve |
| Oleandomycin (100) | −Ve | −Ve | −Ve | −Ve | −Ve | −Ve |
| Lincomycin (100) | −Ve | −Ve | −Ve | −Ve | −Ve | −Ve |
| Penicillin G (10 i.u) | −Ve | −Ve | −Ve | −Ve | −Ve | −Ve |

Growth at different temperature ° C.

| | | | | | | |
|---|---|---|---|---|---|---|
| 4 | − | − | − | − | − | − |
| 10 | ++ | | ++ | ++ | ++ | ++ |
| 20 | ++ | ++ | ++ | ++ | ++ | ++ |
| 28 | ++ | ++ | ++ | ++ | ++ | ++ |
| 37 | ++ | ++ | + | ++ | ++ | ++ |
| 45 | + | ++ | − | ++ | ++ | ++ |

Growth at different pH

| | | | | | | |
|---|---|---|---|---|---|---|
| 2 | − | − | − | − | − | − |
| 5 | ++ | ++ | ++ | ++ | ++ | ++ |
| 7 | ++ | ++ | ++ | ++ | ++ | ++ |
| 9 | ++ | ++ | + | ++ | ++ | ++ |
| 11 | ++ | ++ | − | ++ | ++ | ++ |
| 13 | ++ | ++ | − | ++ | ++ | ++ |

Growth in the presence (% w/v)

| | | | | | | |
|---|---|---|---|---|---|---|
| Control | ++ | ++ | ++ | ++ | ++ | ++ |
| Sodium chloride (1) | ++ | ++ | ++ | ++ | ++ | ++ |
| Sodium chloride (3) | ++ | ++ | ++ | ++ | ++ | ++ |
| Sodium chloride (5) | ++ | ++ | ++ | ++ | ++ | ++ |
| Sodium chloride (7) | − | ++ | ++ | ++ | ++ | ++ |

TABLE 12-continued

Comparative studies of $N_2$ with standard cultures:

| Characters/Tests | $N_2$ | Streptomyces erumpens | Streptomyces albduncus | Streptomyces olivvaceiscleroticus | Streptomyces viridodiastaticus | Streptomyces viridiviolaceus |
|---|---|---|---|---|---|---|
| Sodium chloride (9) | − | ++ | ++ | ++ | ++ | ++ |
| Sodium chloride (11) | − | + | − | ++ | − | − |
| Sodium chloride (13) | − | + | − | ++ | − | − |
| Growth on sole nitrogen source (0.1% w/v) | | | | | | |
| DL-α-Amino-n-butyric acid | ++ | ++ | ++ | ++ | ++ | ++ |
| Potassium nitrate | ++ | ++ | ++ | ++ | ++ | + |
| L-Cysteine | ++ | ++ | ++ | ++ | ++ | + |
| L-Valine | + | ++ | ++ | ++ | ++ | ++ |
| L-Threonine | ++ | ++ | ++ | ++ | ++ | + |
| L-Serine | ++ | ++ | ++ | ++ | ++ | ++ |
| L-Phenylalanine | + | ++ | ++ | ++ | ++ | + |
| L-Lysine | ++ | ++ | ++ | ++ | ++ | + |
| L-Methiionine | ++ | ++ | ++ | ++ | ++ | ++ |
| L-Histidine | ++ | ++ | ++ | ++ | ++ | + |
| L-Arginine | + | ++ | ++ | ++ | ++ | + |
| L-Hydroxy proline | ++ | ++ | ++ | ++ | ++ | + |
| Tryptophan | ++ | ++ | + | ++ | − | + |
| Glutamic acid | ++ | ++ | ++ | ++ | ++ | ++ |
| Tyrosine | ++ | ++ | ++ | ++ | ++ | ++ |
| Ornithine mono HCl | ++ | ++ | ++ | ++ | ++ | ++ |
| Glycine | ++ | ++ | ++ | ++ | ++ | ++ |
| L-Leucine | ++ | ++ | ++ | ++ | ++ | ++ |
| Aspartic acid | − | ++ | − | ++ | − | + |
| Dopa | ++ | − | ++ | ++ | ++ | ++ |
| Alanine | ++ | ++ | ++ | ++ | ++ | + |
| Growth on the sole carbon source (1.0% w/v) | | | | | | |
| L-Arabinose | ++ | ++ | ++ | − | ++ | + |
| Cellulose | + | ++ | + | + | ++ | ++ |
| Sucrose | − | ++ | ++ | ++ | ++ | ++ |
| Starch | ++ | ++ | ++ | ++ | ++ | ++ |
| Sorbitol | ++ | ++ | ++ | ++ | ++ | ++ |
| D-Xylose | ++ | ++ | ++ | ++ | + | ++ |
| meso-Inositol | ++ | ++ | ++ | + | ++ | ++ |
| Mannitol | ++ | + | ++ | + | ++ | ++ |
| D-Fructose | ++ | ++ | ++ | ++ | + | ++ |
| D-Glucose | ++ | ++ | ++ | ++ | ++ | ++ |
| L-Rhamnose | ++ | + | ++ | ++ | ++ | − |
| Raffinose | + | ++ | ++ | + | ++ | ++ |
| Maltose | ++ | ++ | ++ | ++ | ++ | ++ |
| D-Mannose | ++ | ++ | ++ | ++ | + | ++ |
| D-Lactose | ++ | − | ++ | + | + | ++ |
| Inulin | − | + | ++ | ++ | + | + |
| Trehalose | ++ | ++ | ++ | ++ | ++ | + |
| D-Melibiose | ++ | ++ | ++ | + | ++ | ++ |
| Dextran | ++ | ++ | ++ | ++ | + | +++ |
| D-Galactose | ++ | ++ | ++ | − | ++ | ++ |
| Cellobiose | ++ | ++ | ++ | ++ | ++ | ++ |
| Xylitol | + | ++ | ++ | ++ | + | + |
| Sodium acetate (0.1% w/v) | + | + | ++ | + | ++ | ++ |
| Sodium citrate (0.1% w/v) | + | − | ++ | ++ | ++ | ++ |
| Sodium malonate (0/1% w/v) | − | + | + | + | + | + |
| Sodium propionate (0.1% w/v) | + | + | ++ | ++ | ++ | + |
| Sodium pyruvate (0.1% w/v) | + | + | ++ | ++ | ++ | +++ |

TABLE 13

Cultural characteristics on different media:

| Media | N₂ | *Streptomyces erumpens* | *Streptomyces albduncus* | *Streptomyces olivvaceiscleroticus* | *Streptomyces viridodiastaticus* | *Streptomyces viridiviolaceus* |
|---|---|---|---|---|---|---|
| Yeast extract Malt extract agar | | | | | | |
| Growth | Good | Moderate | Good | Good | Good | Good |
| Aerial mycelium | Blackish gray | Gray | Gray | White | Gray | Gray |
| Substrate mycelium | Black | Reddish brown | Reddish brown | Red | Yellowish brown | Reddish brown |
| Soluble pigment | Nil | Nil | Nil | Nil | Nil | Nil |
| Oat meal agar | | | | | | |
| Growth | Good | Good | Moderate | Moderate | Good | Good |
| Aerial mycelium | White | Reddish brown | Gray | White | Gray | Grayish white |
| Substrate mycelium | Dark brown | Brown | Colorless | Pink | Colorless | Blackish yellow |
| Soluble pigment | Nil | Nil | Nil | Nil | Nil | Nil |
| Inorganic salt and starch agar | | | | | | |
| Growth | Good | Moderate | Moderate | Moderate | Good | Good |
| Aerial mycelium | Grayish white | Colorless | White | White | Gray | Whitish gray |
| Substrate mycelium | Reddish brown | Reddish brown | Reddish brown | Colorless | Yellowish brown | Brown |
| Soluble pigment | Nil | Nil | Nil | Nil | Nil | Nil |
| Glycerol aspargine agar | | | | | | |
| Growth | Good | Moderate | Good | Moderate | Good | Good |
| Aerial mycelium | Grayish white | Gray | White | Colorless | Gray | Gray |
| Substrate mycelium | Blackish brown | Colorless | Reddish brown | Yellow | Colorless | Gray |
| Soluble pigment | Nil | Nil | Nil | Nil | Nil | Nil |
| Peptone yeast extract iron agar | | | | | | |
| Growth | Moderate | Moderate | Good | Good | Moderate | Moderate |
| Aerial mycelium | Grayish black | Yellowish brown | Whitish gray | Pinkish white | Gray | Gray |
| Substrate mycelium | Gray | Yellow | Colorless | Pink | Colorless | Yellow |
| Soluble pigment | Nil | Nil | Nil | Nil | Nil | Nil |
| Tyrosine agar | | | | | | |
| Growth | Good | Moderate | Moderate | Moderate | Good | Good |
| Aerial mycelium | Grayish black | White | White | Pink | Gray | Grayish white |
| Substrate mycelium | Gray | Colorless | Colorless | Colorless | Colorless | Pinkish yellow |
| Soluble pigment | Nil | Nil | Nil | Nil | Nil | Nil |
| Starch casein agar | | | | | | |
| Growth | Good | Good | Good | Moderate | Good | Moderate |
| Aerial mycelium | Gray | Gray | Gray | Colorless | Grayish white | Gray |
| Substrate mycelium | White | White | Colorless | Pink | Colorless | Yellow |
| Soluble pigment | Nil | Nil | Nil | Nil | Nil | Nil |
| Potato dextrose agar | | | | | | |
| Growth | Good | Good | Good | Moderate | Good | Good |
| Aerial mycelium | Grayish white | White | Whitish gray | Colorless | White | Grayish white |
| Substrate mycelium | Dirty green | Yellowish brown | Brown | Colorless | Colorless | Blackish yellow |
| Soluble pigment | Nil | Nil | Nil | Nil | Nil | Nil |

TABLE 13-continued

Cultural characteristics on different media:

| Media | Streptomyces N₂ | Streptomyces erumpens | Streptomyces albduncus | Streptomyces olivvaceiscleroticus | Streptomyces viridodiastaticus | Streptomyces viridiviolaceus |
|---|---|---|---|---|---|---|
| Nutrient agar | | | | | | |
| Growth | Moderate | Moderate | Good | Moderate | Moderate | Good |
| Aerial mycelium | White | White | White | White | Colorless | Grayish white |
| Substrate mycelium | Colorless | Colorless | Colorless | Colorless | Colorless | Yellowish brown |
| Soluble pigment | Nil | Nil | Nil | Nil | Nil | Nil |
| Glucose aspargine agar | | | | | | |
| Growth | Good | Moderate | Good | Moderate | Moderate | Good |
| Aerial mycelium | Grayish black | White | White | Colorless | White | Grayish white |
| Substrate mycelium | Colorless | Colorless | Reddish brown | White | Colorless | Yellow |
| Soluble pigment | Nil | Nil | Nil | Nil | Nil | Nil |
| Bennets agar | | | | | | |
| Growth | Moderate | Moderate | Good | Moderate | Moderate | Moderate |
| Aerial mycelium | Colorless | White | White | White | Golden yellow | Colorless |
| Substrate mycelium | Colorless | Reddish brown | Reddish brown | Colorless | Golden yellow | Colorless |
| Soluble pigment | Nil | Reddish brown | Nil | Nil | Nil | Nil |
| Czapek dox agar | | | | | | |
| Growth | Good | Moderate | Good | Moderate | Good | Moderate |
| Aerial mycelium | Gray | Gray | Gray | White | Grayish white | White |
| Substrate mycelium | White | Colorless | Brown | Colorless | Pale yellow | Yellow |
| Soluble pigment | Nil | Nil | Nil | Nil | Nil | Nil |

ADVANTAGES

1. The compound Nonadeca-6-enoic acid-3-(hexadecyloxy-hydroxy-thiophosphoryloxy)-quinoxalin-2-yl ester, designated as streptolipin, useful for pancreatic lipase inhibition, isolated from the culture of *Streptomyces vayuensis* strain N₂, is novel.
2. The process is novel because the culture '*Streptomyces vayuensis* strain N₂' and the product Nonadeca-6-enoic acid-3-(hexadecyloxy-hydroxy-thiophosphoryloxy)-quinoxalin-2-yl ester obtained in the process are novel.
3. The said compound is used for the preparation of pharmaceutical composition.
4. The said pharmaceutical composition is useful particularly for prevention of obesity and treatment of disorders of the central nervous system; damage to the central nervous system; cardiovascular disorders; gastrointestinal disorders; diabetes and sleep apnea.
5. The said pharmaceutical composition used in the form of oral, parental, buccal and ocular administration.

We claim:

1. A compound of Formula I:

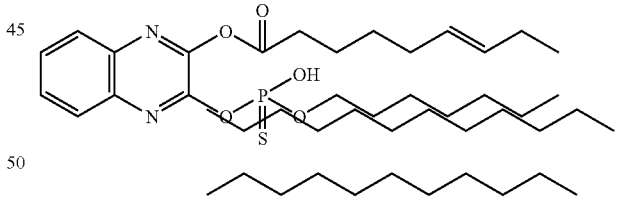

Formula 1 or a pharmaceutically acceptable salt thereof.

2. A pharmaceutical composition comprising a compound according to claim 1, or a pharmaceutically acceptable salt thereof, and a pharmaceutically acceptable excipient.

* * * * *